(12) United States Patent
Bommarito et al.

(10) Patent No.: US 12,350,395 B2
(45) Date of Patent: Jul. 8, 2025

(54) PROCESS AND DEVICE FOR GENERATING A MOVING FRONT WITHIN A STERILIZATION MONITORING DEVICE AND USES THEREOF

(71) Applicant: Solventum Intellectual Properties Company, Maplewood, MN (US)

(72) Inventors: G. Marco Bommarito, Stillwater, MN (US); Scott D. Anderson, Lakeland, MN (US); Ryan W. Clarke, Woodbury, MN (US); Paul N. Holt, St. Paul, MN (US); William E. Foltz, Cottage Grove, MN (US); Timothy J. Nies, Stillwater, MN (US); Kevin D. Landgrebe, Woodbury, MN (US); Jeffrey D. Cotton, St. Paul, MN (US); Ryan T. Woldt, Minneapolis, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 910 days.

(21) Appl. No.: 17/594,183

(22) PCT Filed: Dec. 17, 2019

(86) PCT No.: PCT/IB2019/060945
§ 371 (c)(1),
(2) Date: Oct. 6, 2021

(87) PCT Pub. No.: WO2020/217093
PCT Pub. Date: Oct. 29, 2020

(65) Prior Publication Data
US 2022/0160920 A1     May 26, 2022

Related U.S. Application Data

(60) Provisional application No. 62/839,446, filed on Apr. 26, 2019.

(51) Int. Cl.
*A61L 2/28* (2006.01)
*G01N 31/22* (2006.01)
*A61L 2/20* (2006.01)

(52) U.S. Cl.
CPC ................ *A61L 2/28* (2013.01); *G01N 31/22* (2013.01); *A61L 2/208* (2013.01)

(58) Field of Classification Search
CPC ........... A61L 2/208; A61L 2/28; G01N 31/22; G01N 31/226
See application file for complete search history.

(56) References Cited

U.S. PATENT DOCUMENTS

| 4,138,216 A | 2/1979 | Larsson |
| 4,145,186 A | 3/1979 | Anderson |

(Continued)

FOREIGN PATENT DOCUMENTS

| CN | 207562134 U | 7/2018 |
| CN | 207722140 U | 8/2018 |

(Continued)

OTHER PUBLICATIONS

International Search Report for PCT International Application No. PCT/IB2019/060945, mailed on Jun. 25, 2020, 4 pages.

*Primary Examiner* — Timothy C Cleveland

(57) ABSTRACT

The disclosed sterilization monitoring device comprises a perfusion channel with a chemical indicating composition disposed in fluid communication with the perfusion channel. Exposure to a sterilant creates a laterally moving front across the chemical indicating composition in the perfusion channel.

15 Claims, 11 Drawing Sheets

(56) References Cited

U.S. PATENT DOCUMENTS

| | | |
|---|---|---|
| 4,579,715 A | 4/1986 | Bruso |
| 5,872,004 A | 2/1999 | Bolsen |
| 6,485,979 B1 | 11/2002 | Kippenhan |
| 6,897,059 B2 | 5/2005 | Foltz |
| 7,045,343 B2 | 5/2006 | Witcher |
| 7,247,482 B2 | 7/2007 | Lemus |
| 7,481,975 B2 | 1/2009 | Read |
| 7,927,866 B2 | 4/2011 | Justi |
| 8,343,768 B2 | 1/2013 | Kyung-Hee Song et al. |
| 9,017,994 B2 | 4/2015 | Franciskovich |
| 10,119,946 B2 | 11/2018 | Bala et al. |
| 10,947,577 B2 | 3/2021 | Ahimou et al. |
| 2003/0215923 A1 | 11/2003 | Witcher |

FOREIGN PATENT DOCUMENTS

| | | |
|---|---|---|
| EP | 0428245 | 5/1991 |
| EP | 2362786 | 9/2011 |
| WO | WO2002-087639 | 11/2002 |
| WO | WO2020-128956 | 6/2020 |

PROCESS AND DEVICE FOR GENERATING A MOVING FRONT WITHIN A STERILIZATION MONITORING DEVICE AND USES THEREOF

CROSS REFERENCE TO RELATED APPLICATIONS

This application is a national stage filing under 35 U.S.C. 371 of PCT/IB2019/060945, filed Dec. 17, 2019, which claims the benefit of U.S. Provisional Application No. 62/839,446, filed Apr. 26, 2019, the disclosure of which is incorporated by reference in its/their entirety herein.

TECHNICAL FIELD

The present disclosure relates to sterilization monitoring devices and methods of using the sterilization monitoring devices thereof.

BACKGROUND

Many objects require sterilization prior to their use. One example of such objects includes medical devices. Typically, medical devices are sterilized in sterilization processes that employ a sterilant, such as steam or other sterilizing liquids and gases. Sterilization employing steam is achieved by exposing objects to pressurized saturated steam at elevated temperatures for a sufficient duration of time. Other sterilization processes may employ the use of chemicals in liquid or gas phase. Two typical chemical sterilants are hydrogen peroxide and ethylene oxide, the former typically being employed in the vaporized form.

Sterilization processes employing vaporized hydrogen peroxide (VHP) can be operated at lower temperatures and typically for shorter durations than the ethylene oxide counterpart or other forms of sterilization. Lower temperatures are typical, especially for heat-sensitive objects, such as those comprising heat-sensitive plastic or other heath-sensitive materials.

It is critical to accurately assess and monitor the sufficiency of the sterilization process to ensure complete sterilization of the objects. Several methods of sterilization monitoring are employed. One method involves the use of sterilization indicators. Sterilization indicators typically include a chemical indicating composition carried on a substrate. Chemical indicating compositions are typically substances that give a visible sign of reaction (typically a color change) that indicates that a threshold level of reactant (such as, for example, a sterilant) was present during the sterilization process.

Sterilization process indicators monitor a single sterilization parameter, typically exposure to a threshold level of sterilant (sterilant concentration), regardless of time, temperature and/or other parameters. Sterilization multi-parameter indicators, on the other hand, monitor multiple critical sterilization parameters and indicate whether the objects subjected to the sterilization process been exposed sufficiently to sterilant to meet more than one of the critical parameters for sterilization (typically duration of exposure to sterilant, concentration of sterilant, and temperature of sterilant). Sterilization integrators, monitor all critical parameters for a given sterilization modality, and indicate whether the objects subjected to the sterilization process been exposed sufficiently to sterilant to meet all of the critical parameters for sterilization.

Since sufficient sterilization in a given sterilization cycle is typically dependent upon more than one parameter, it is advantageous to provide monitoring technology that is capable of indicating whether all critical sterilization parameters have been met. Sterilization integrators closely mimic the response of biological indicators (the gold standard of sterilization monitoring) but are significantly less expensive and may require less time to obtain results. Therefore, the availability of a sterilization integrator for any given sterilization process is highly desirable. Furthermore, it is desirable that a sterilization monitors yield results that are clear, accurate, and easy to read.

SUMMARY

The disclosed sterilization monitoring device comprises a perfusion channel with a chemical indicating composition disposed in fluid communication with the perfusion channel Exposure to a sterilant creates a laterally moving front across the chemical indicating composition in the perfusion channel.

In some aspects the present disclosure is directed to a sterilization monitoring device comprising at least one perfusion channel comprising a first end and a second end, wherein at least one of the first or second end are open to the environs, wherein the channel comprises a height, width and a length, and at least one chemical indicting composition disposed in fluid communication with the at least one perfusion channel and extending along at least a portion of the at least one perfusion channel, wherein the perfusion channel creates a laterally moving front of a sterilant across the chemical indicating composition.

In other aspects the present disclosure is related to a chemical indicator chemical indicating composition carrier housing comprising at least one perfusion channel defining a fluid pathway, the perfusion channel comprising a height, a width, and a length extending between a first end and a second end, wherein at least one of the first and second ends is in fluid communication with the environs, a chemical indicating composition carrier retainer configured to the chemical indicating composition carrier wherein the retainer comprises an upper portion comprising at least one upper chemical indicating composition carrier contacting region, wherein the chemical indicating composition carrier retainer is configured to receive the chemical indicating composition carrier such that a region printed with a chemical indicating composition is in fluid communication with at least a portion of the perfusion channel.

In other aspects the present disclosure is related to a process for generating a moving front of chemical indicating composition in response to a sterilization process comprising the steps of: providing a sterilization monitoring device comprising at least one perfusion channel comprising a height, a width, and a length extending between a first end and a second end, wherein at least one of the first or second ends are open to the environs, at least one chemical indicating composition disposed in fluid communication with the at least one perfusion channel and extending along at least a portion of the at least one perfusion channel, exposing the sterilization monitoring device to a sterilant, wherein the sterilant enters the perfusion channel through at least one of the first or second ends, wherein the perfusion channel creates a moving front of sterilant through the perfusion channel, and reacting the sterilant with the chemical indicating composition to create a moving front of reacted chemical indicating composition.

BRIEF DESCRIPTION OF THE DRAWINGS

FIG. 6b is an end view of the embodiment of FIG. 6a.

FIG. 6c is a top view of the embodiments of FIG. 6a.

Figure 1A:
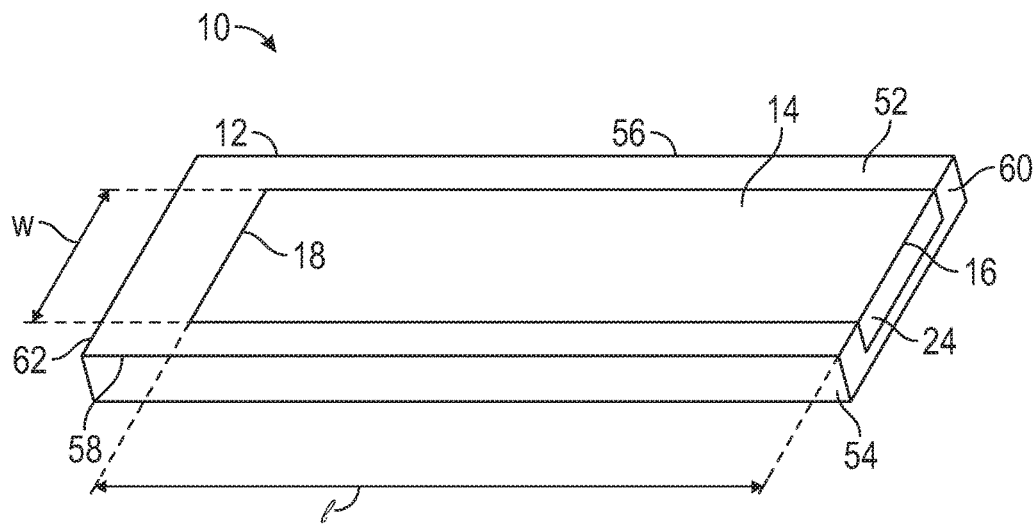
FIG. 1a is perspective view of an embodiment of a sterilization monitoring device of the present disclosure.

While the above-identified drawings and figures set forth embodiments of the invention, other embodiments are also contemplated, as noted in the discussion. In all cases, this disclosure presents the invention by way of representation and not limitation. Numerous other modifications and embodiments can be devised by those skilled in the art, which fall within the scope and spirit of this invention. The figures may not be drawn to scale.

DETAILED DESCRIPTION

All scientific and technical terms used herein have meanings commonly used in the art unless otherwise specified. The definitions provided herein are to facilitate understanding of certain terms used frequently in this application and are not meant to exclude a reasonable interpretation of those terms in the context of the present disclosure.

Unless otherwise indicated, all numbers in the description and the claims expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The term "substantially impermeable" as used herein refers to the relative inability of sterilant gas to penetrate a sheet of the chemical indicator. The goal of using substantially impermeable material is to prevent the transport of sterilant, such as hydrogen peroxide, across the material so that sterilant is only transported via the opening and corresponding channel to the chemical-indicating composition. In some embodiments, the material allows transport of sterilant across a sheet of less than 5% of the sterilant flowing across the opening during the sterilization cycle. In other embodiments, the material allows transport of sterilant across a sheet of less than 1%, or less than 0.5%, or less than 0.1% of the sterilant flowing across the opening during the sterilization cycle. An indicator of the present disclosure comprising substantially impermeable first and second sheets allows sterilant gas to move along the fluid pathway and contact the chemical-indicating composition and does not allow sterilant gas to contact the chemical-indicating composition by traversing the first and second sheets. As such, a test for substantial impermeability of a sheet of the disclosure can be made by blocking entrance of sterilant gas to the opening(s) of the fluid pathway(s) of the indicator of the present disclosure; if the color of the indicator changes by exposure of such a modified indicator to sterilant gas after completion of a sterilization cycle, then the sheets are not considered to be substantially impermeable for the purposes of the present disclosure.

The term "substantially along the entire length" of an element (e.g., a perfusion channel) refers to a length that is within 10% of the total length of the element. For example, a chemical indicating composition that extends substantially along the entire length of a channel refers to a length of chemical indicating composition that is within 10% of the total length of the channel.

The terms "channel" and "perfusion channel" are used interchangeably herein.

The following disclosure will be described within the context of sterilization processes for medical instruments. However, it will be appreciated that the sterilization monitoring devices of the present disclosure may be used in any variety of sterilization processes for the sterilization of any object.

Medical instruments are typically prepared for sterilization by placement into packs, trays, containers, or peel pouches. The instruments thus prepared are loaded into the chambers of sterilization equipment and subjected to an appropriate sterilization cycle. Successful sterilization is dependent upon multiple factors including proper pack assembly, proper loading of the sterilization chamber and exposure to sterilization cycles that provide threshold levels of critical sterilization parameters such as, duration, temperature, and concentration of sterilant.

Generally, three different types of sterilant employed: ethylene oxide, vaporized hydrogen peroxide (VHP), and steam. However, it will be appreciated that the present sterilization monitoring devices are not limited to use with any particular sterilant. The present sterilization monitoring devices can be adapted to be compatible with any sterilant and/or other critical sterilization parameter.

The particular sterilant employed may be determined by a number of factors including the temperature-sensitivity/resistance of the instruments. In all cases, the sterilization process must be capable of being monitored in some fashion so that the efficacy of the sterilization cycle can be assessed. If incomplete sterilization occurs, the technician or operator must be made aware to avoid using improperly sterilized instruments in a surgical procedure and to initiate reprocessing of the instruments by subjecting them to an additional sterilization cycle.

Options for monitoring sufficiency of sterilization include chemical indicators, chemical integrators, and biological indicators. Biological indicators (BI) are considered to be the most accurate because they indicate the level of lethality achieved during a sterilization cycle, but also are the most expensive and time consuming since the BI must be incubated a sufficient amount of time to allow for proliferation of any surviving spores. Chemical integrators, which monitor all critical sterilization parameters are considered to be nearly as accurate as BIs and are far more cost effective. Applicant is unaware of any chemical integrator suitable for use with VHP. Desirably, the present inventive sterilization monitoring device is suitable for use as an integrator for VHP sterilization (as well as other sterilants).

Ease of use and clarity of results are essential to accurately assess efficacy of a sterilization cycle, thus ensuring that medical instruments are safely sterilized. Typically, "moving front" technology is considered to be a reliable indicator. In typical prior art moving front technology, the chemical indicating composition undergoes a phase change in response to critical sterilization parameters and migrates laterally along a given substrate, typically by diffusion and/or wicking. The distance the chemical indicating composition migrates is correlated with critical sterilization parameters. The threshold distance of migration (i.e., the minimum distance the front travels under sufficient levels of all critical sterilization parameters) determines whether the sterilization cycle was successful. An example of such technology is described in U.S. Pat. Nos. 6,485,979 and 4,138,216, the disclosures of which are herein incorporated. Due to the specific chemistries of the chemical indicating compositions used with VHP, moving front technology has been previously unknown. The disclosed sterilization monitoring devices introduce novel concepts making moving front technology possible with a variety of sterilants, including, advantageously, VHP.

Various embodiments of the invention will now be described with reference to the accompanying drawings.

Figure 1B:
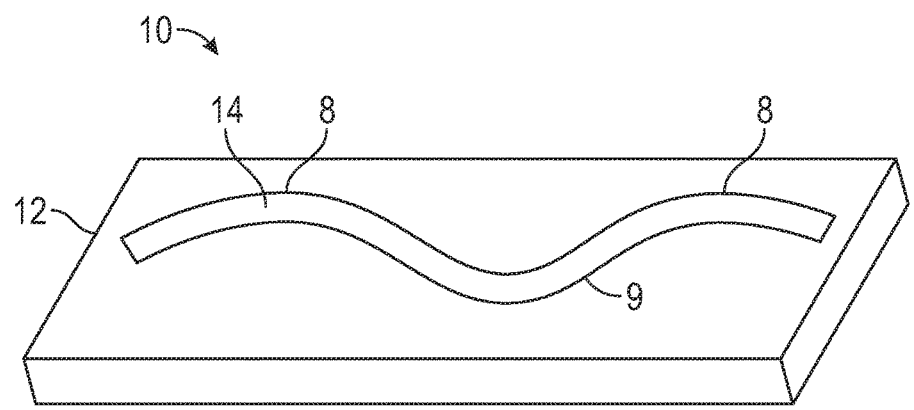
FIG. 1b is a perspective view of an embodiment of a sterilization monitoring device of the present disclosure.
Figure 2:
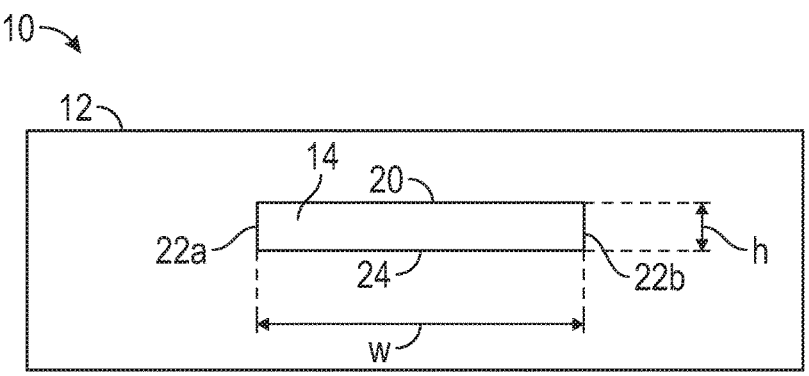
FIG. 2 is an end view of the embodiment depicted in FIG. 1.
Figure 3A:
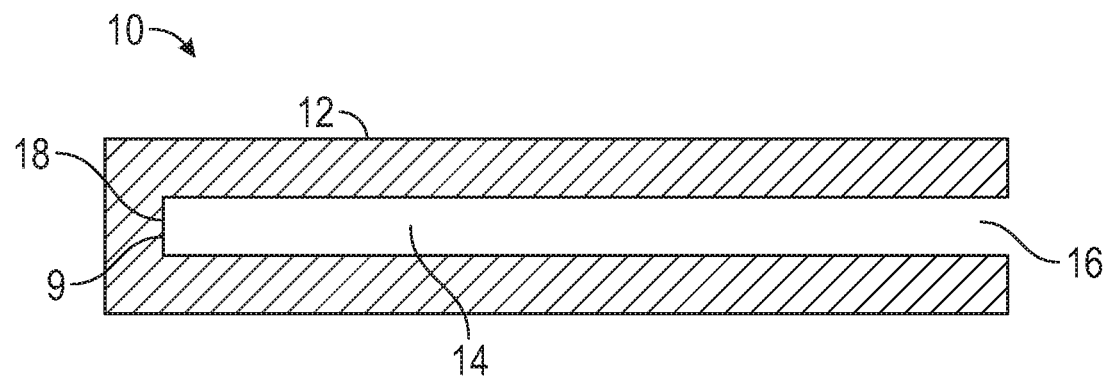
FIG. 3a is cross section of a side view of the embodiment depicted in FIG. 1.

FIGS. 1-3 depict various views of an embodiment of the sterilization monitoring device according to the present disclosure. FIG. 1 is a perspective view of an embodiment of a sterilization monitoring device 10 according to the present disclosure. FIG. 2 is end view of the embodiment shown in FIG. 1. FIG. 3a is cross sectional side view of the embodiment depicted in FIGS. 1 and 11.

Sterilization monitoring device 10 comprises a housing 12 provided with at least one perfusion channel 14 having a length l that extends between a first end 16 and a second end 18. Perfusion channel 14 further comprises a width, w and height, h, more clearly shown in FIG. 2.

The particular configuration and properties of the housing 12 are inconsequential so long as the specifics related to the perfusion channel (described in detail below) can be accommodated. The only requirement is that the housing 12, regardless of its form, substantially isolates the perfusion channel 14 from the environs except at portions that are intentionally configured to be in fluid communication with the environs (discussed in detail below).

In the embodiment illustrated, housing 12 comprising an upper portion 52, a bottom portion 54, and two side edges 56, 58 extending between two end edges 60, 62. In some embodiments, upper portion 52 comprises at least a portion that is transparent, through which at least a portion of the perfusion channel 14 is visible from the exterior of the housing 12. Upper 52 and/or lower portion 54 may carry a variety of markings and/or labels displaying identifying marks and/or other information useful to a user. In some embodiments, upper portion 52 includes indicia useful for interpreting results. Such indicia may include hashmarks, for example. Other indicia are within the scope of the present disclosure.

Housing may comprise a molded piece comprised of plastic or other material that can withstand the sterilization process conditions and is substantially impervious to the sterilant. Alternately, the housing may be a laminated assembly comprised of multiple layers as described in U.S. App. No. 62/783,764 filed on Dec. 21, 2018, the disclosure of which is herein incorporated by reference. Various housing configurations and designs may be employed and readily arrived at by those of skill in the art. Alternately, housing may comprise a combination of one or more molded pieces and one or more films or membranes.

Perfusion channel 14 comprises a ceiling portion 20 that extends from the first end 16 to the second end 18. Two side walls 22a, 22b extend from the ceiling portion 20 and define a height, h of the perfusion channel 14. In the embodiment shown in the Figures, perfusion channel 14 terminates at the second end 18 at a terminal wall 19 (shown in FIG. 3a).

Figure 3B:
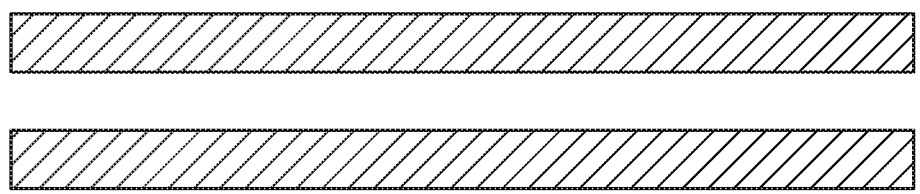
FIG. 3b is cross section of a side view of an embodiment of the sterilization monitoring device of the present disclosure.

Perfusion channel 14 comprises at least one open end in fluid communication with the environs. In the embodiments shown in FIGS. 1 and 3a, the first end 16 is open and is in fluid communication with the environs. In alternate embodiments, one of which is shown in FIG. 3b, the terminal wall 19 is omitted and both the first end 16 and the second end 18 are in fluid communication with the environs. In the embodiments depicted, the open end 16 is shown to be in direct contact with the environs. However, in alternate embodiments, the open end may be covered by a film, membrane, or other material that is pervious to the sterilant being employed. Alternately, the open end may be coupled to an additional structure. So long as the structure allows fluid communication between the open end and the environs, any configuration is within the scope of the present disclosure.

Figure 3C:
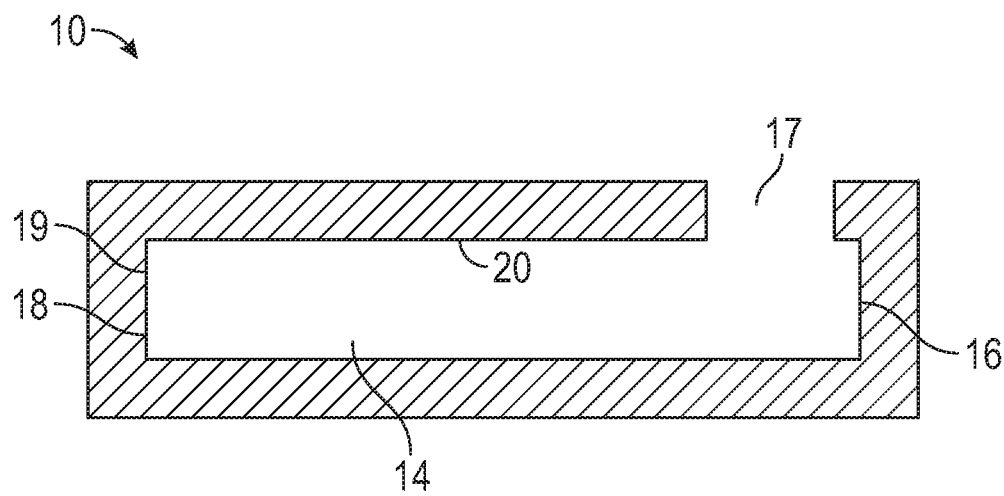
FIG. 3c is a cross section side view of a sterilization monitoring device according to an embodiment of the present disclosure.

In the embodiments shown in the Figures, the open end of the perfusion channel is shown to be disposed at the terminus of the channel. It will be appreciated that other configurations are within the scope of the present disclosure. For example, as shown in FIG. 3c, in some embodiments an open end 17 is disposed within ceiling portion 20 of channel 14. In these embodiments, open end may be disposed at terminus of perfusion channel or at any location along (not shown) the perfusion channel dependent upon the specific sterilization conditions and/or channel dimensions. Any placement of the open end that achieves the desired sterilant perfusion rate is within the scope of the present disclosure.

Likewise, the perfusion channel is shown in majority of Figures to be linear. However, as shown in FIG. 1b, channel 14 may comprise one or more curves 8, turns, constrictions 9, or other characteristics. It will be appreciated that all conceivable channel characteristics that achieve the desired sterilant perfusion rate are within the scope of the present disclosure.

The perfusion channel 14 is shown in the Figures to be integral to the housing 12 such that housing 12 defines a floor portion 24 of the perfusion channel 14. However, as will be appreciated by those of skill in the art, floor portion may be configured in a variety of manners. For example, perfusion channel 14 can be provided as a separate component that either functions independently (discussed below and shown in FIG. 4) or is inserted into a housing (not shown).

Figure 4:
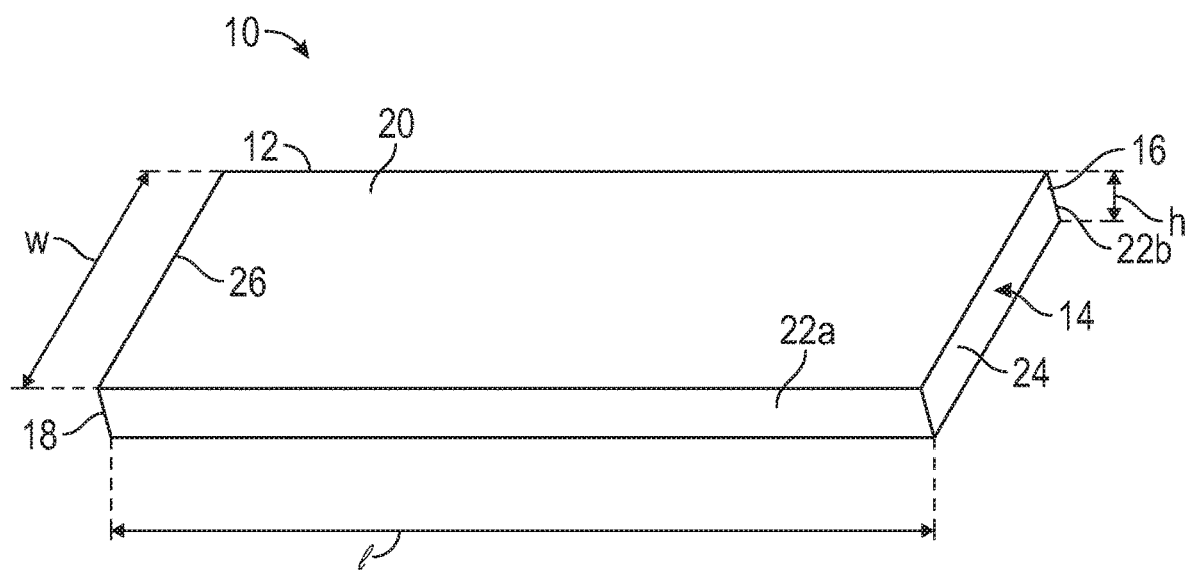
FIG. 4 is a perspective view of another embodiment of the sterilization monitoring device of the present disclosure.

An alternate embodiment of the sterilization monitoring device is provided in perspective view in FIG. 4. In this embodiment, the housing 12 defines the ceiling portion 20, side walls 22a, 22b, and floor portion 24 as well as the terminal end portion 26. Housing is comprised of a material, such as a variety of plastics or other materials that can withstand sterilization conditions and provide a substantially impervious barrier so that the channel interior is isolated from exposure to the environs/sterilant. This embodiment could also serve as a cartridge that may be inserted into a larger housing.

Perfusion channel 14 is engineered to produce a channel interior having a height and width that is substantially constant along at least of the portion of the length of the perfusion channel 14 length. Perfusion channel 14 defines a fluid pathway for lateral flow of sterilant from the environs through perfusion channel interior 26 in a direction extending away from the open end. As will be discussed in detail below, lateral flow through the perfusion channel 14 can be accomplished by engineering any combination of the perfusion channel dimensions (height, width, and/or length) to induce flow in through the open end and to continue a lateral flow path across perfusion channel length when the sterilization monitoring device 10 is subjected to a pressure differential creating a pressure gradient extending from the environs to the channel interior 26. Advantage can be taken of the typical steps in sterilization processes to generate a lateral flow of sterilant across the perfusion channel.

In a typical sterilization process, instruments and sterilization monitoring devices are loaded into the sterilization chamber of the sterilization equipment. After loading is complete, the chamber is sealed and the air is evacuated from the chamber, creating a vacuum. Upon attainment of a vacuum the sterilization instrument creates the critical sterilization parameters, which, are dependent upon sterilant type and sterilization cycle particulars. Since the chamber is sealed, the pressure within it will increase as the temperature and concentration of sterilant increases. This pressure increase creates a pressure gradient force extending from the environs (the chamber interior) across the perfusion channel 14 of the sterilization monitoring device 10. Therefore, the pressure gradient force will move sterilant, for example, VHP, from the higher-pressure environs of the chamber interior into the lower-pressure environment of the perfusion channel 14 if the channel is appropriately dimensioned.

Appropriate dimensions can be calculated by those of skill in the art by applying the mathematical principles related to laminar flow confined to tubes. Laminar flow rate through a tube can be calculated with the following formula:

$$Q = \frac{P_2 - P_1}{R}$$

Where Q is flow rate, $P_1$ is the pressure external of the perfusion channel, $P_2$ is the pressure within the perfusion channel, and R is the resistance to flow.

The resistance, R, may be approximated applying the principles of Poiseuille's Law, which gives R by the following equation:

$$R = \frac{8nl}{\pi r^4}$$

Where n is the viscosity of the fluid moving through the tube, r is the radius and l is the length. Those of skill in the art will recognize that it may be necessary to account for other factors such as, e.g., sterilizer size and/or sterilization cycle characteristics to achieve suitable lateral flow rates.

In some embodiments, the aspect ratio is the ratio of the width to the height (W/H) of the perfusion channel(s) are at least 4 (4:1) and may range up to 125:1. In some embodiments the length ranges from about 2 cm to about 10 cm. In some embodiments the width ranges from about 0.3 cm to about 1.25 cm. In some embodiments the width is at least about 0.3 cm. In some embodiments the height ranges from about 0.025 mm to about 0.25 cm. In some embodiments the height is at least 0.025 mm. In some embodiments, the length is about 10 cm or less. In some embodiments the length ranges from about 2 cm to about 10 cm. As can be appreciated from the foregoing equations, the dimensions of the perfusion channel (as well as factors related to details of any particular sterilization cycle) can be altered to control the rate at which sterilant flows through the perfusion channel.

Figure 5A:
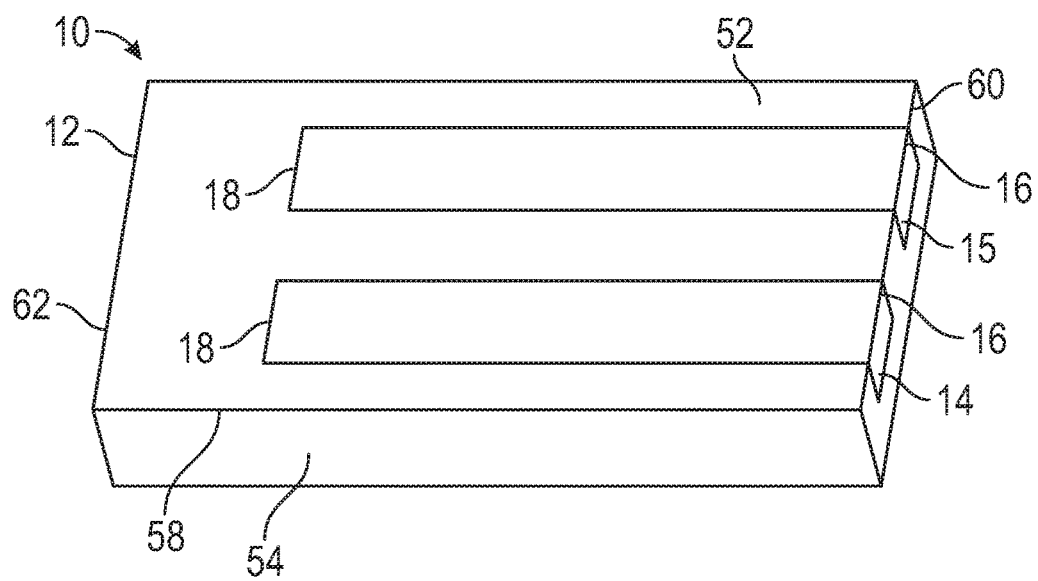
FIG. 5a is a perspective view of an embodiment of the sterilization monitoring device according to the present disclosure.

In some embodiments, an example of one of which is depicted in FIG. 5a, the sterilization monitoring devices comprise more than one channel. In the embodiment shown, the sterilization monitoring device 10 comprises a first and second perfusion channel 14, 15. It will be appreciated, that any number of perfusion channels may be provided. For example, sterilization monitoring device may comprise, 3, 4, 5, or more separate perfusion channels.

Figure 5B:
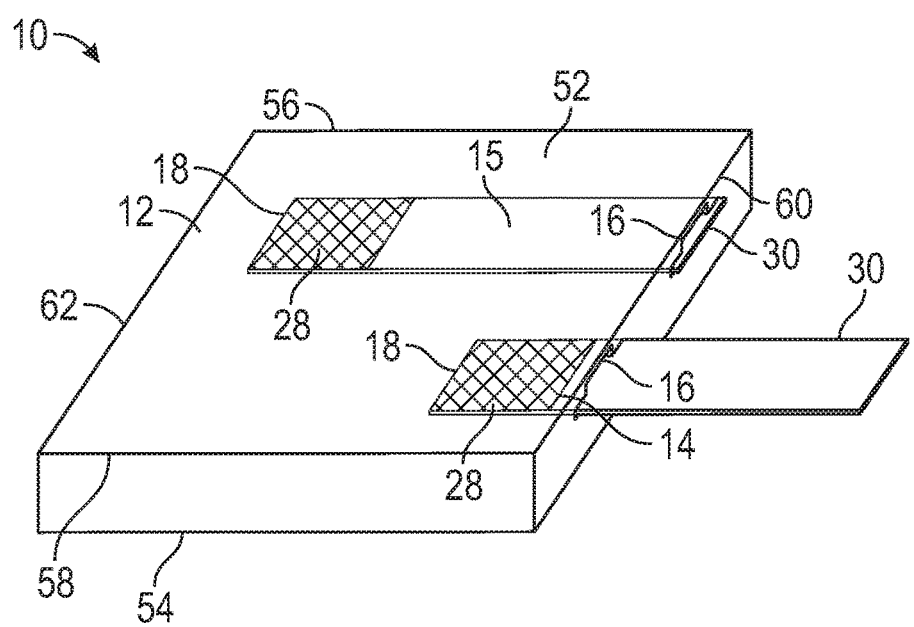
FIG. 5b is a perspective view of an embodiment of the sterilization monitoring device according to the present disclosure.

In embodiments featuring multiple perfusion channels, any combination of channel dimensions is possible. For example, two or more perfusion channels may be engineered to have identical dimensions. In the embodiment shown in FIG. 5a, each of first and second perfusion channels 14, 15 have substantially identical lengths and widths. In the embodiment shown in FIG. 5b, first and second perfusion channels, 14, 15, respectively, are shown to be of a different length. This embodiment is shown with a chemical indicating composition carriers carrying chemical indicating composition 28 disposed in fluid communication with the perfusion channels 14, 15.

Alternately, dimensions of perfusion channels may different from one another in any conceivable number of combinations. For example, perfusion channels may be provided have substantially identical widths and heights but with varying lengths. Alternately, perfusion channels may have varying heights but identical lengths. Alternately, each perfusion channel may be of a unique h, w, and l. In other embodiments, some of the perfusion channels may have substantially identical dimensions while others have different dimensions. Any number of perfusion channels with any number of possible dimensional combinations that are possible and within the scope of the present disclosure.

Figure 5C:
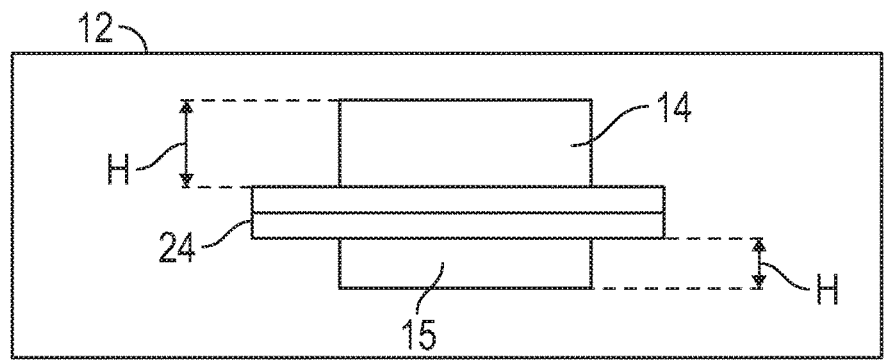
FIG. 5c is an end view of an embodiment of the sterilization monitoring device according to the present disclosure.

A variety of spatial relationships between multiple perfusion channels is contemplated. For example, in the embodiment shown in FIG. 5a, perfusion channels are shown to be disposed side by side in a linear fashion. In the embodiment depicted in FIG. 5c the channels are stacked on top of each other and are dimensioned such that one perfusion channel 14 has a greater height than the other 15. As will be appreciated, dependent upon the particular need and sterilization cycle parameters, any combination of spatial relationships and dimensions of perfusion channels are possible.

Figure 6A:
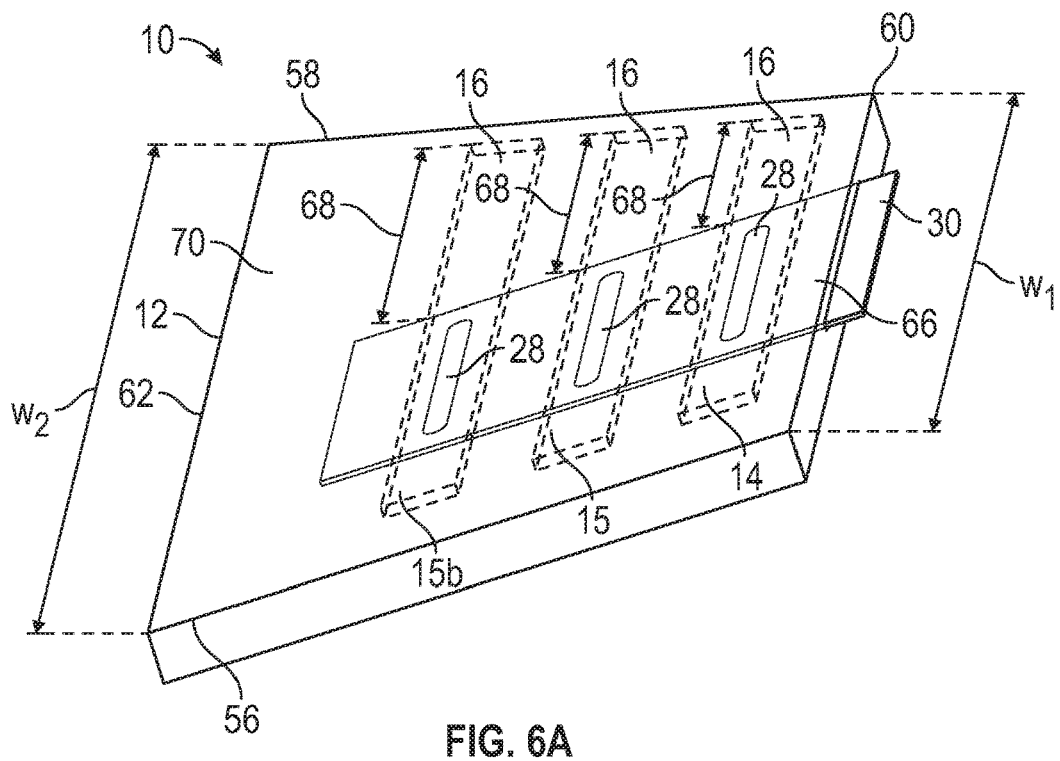
FIG. 6a is a perspective view of an embodiment of the sterilization monitoring device according to the present disclosure.
Figure 6B:
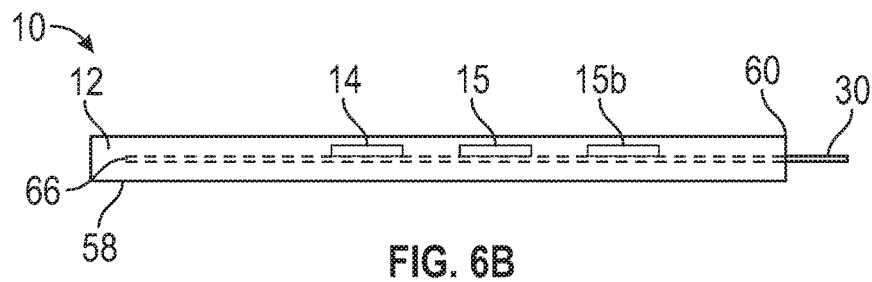
Figure 6C:
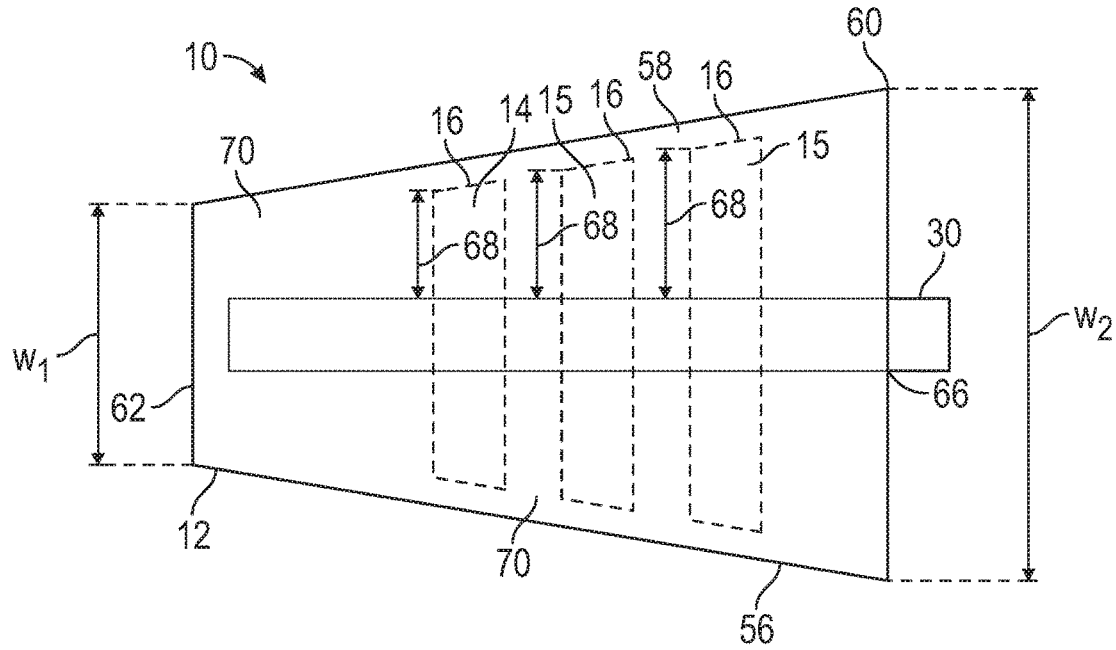

FIGS. 6a-c depict various views of yet another embodiment of a sterilization monitoring device according to the present disclosure. Housing 12 is shown to have a width, $W_1$ at the first housing end 60 that extend between first and second housing edges 56, 58 and a width $W_2$ at the second housing end 62. Second housing end width $W_2$ is greater than $W_1$.

In this embodiment, three perfusion channels, 14, 15, and 15b are shown to disposed in a linear array along second housing edge 58 at regular spacing intervals (i.e., distance between each channel is substantially identical). Channels 14, 15, 15b can also be disposed along first housing edge 56. Similarly, channels may be provided at irregular spacing intervals or a combination of regular and irregular intervals. In some embodiments, at least a portion of an upper portion 70 of housing 12 is transparent so that at least a portion of at least one perfusion channel 14, 15, or 15b is visible from the exterior so that a user may observe the underlying chemical indicating composition 28 within the channel. In another embodiment, the substantially entire upper portion 70 may be transparent. Upper portion 70 may include markings such as branding and/or indicia useful for interpreting results In the embodiment shown, chemical indicating composition is provided on a chemical indicating composition carrier 30 that is retained in a chemical indicating composition carrier retainer 66. Retainer traverses each perfusion channel 14, 15, 15b perpendicular to the length of the channel Retainer 66 typically is constructed in a manner to substantially eliminate perfusion of sterilant therethrough. In any embodiment, perfusion of sterilant through retainer 66 should be minimal enough so as not to contribute in any significant way to reaction of chemical indicating composition. Sterilant entering the channel via perfusion through open end 16 and through channel length should be only significant source of sterilant flowing over chemical indicating composition.

Chemical indicator composition carriers are provided with chemical indicating composition 28 disposed along substantially entire length such that when inserted discrete portions thereof land within each perfusion channel Alternately, chemical indicating composition may be provided at discrete regions that correspond to the location of each perfusion channel.

A perfusion length 68 is defined by the distance extending from the open end (first end 16 in the embodiment depicted) to the chemical indicating composition 28. This is the distance that sterilant must travel before it encounters the chemical indicating composition 28.

As will be appreciated, selective dimensioning of the housing 12 allows for the provision of a single device with multiple perfusion lengths. For example, in the embodiment shown, provision of a generally trapezoid shaped housing 12 (shown most clearly in FIG. 6c), having a second end width $W_1$ that is greater than the first end width $W_2$ allows for perfusion channels 14, 15, 15b having progressively increasing perfusion lengths 68. As will be appreciated, housing can be dimensioned in any number of manners to produce any desired combination of perfusion lengths. For example, housing and corresponding perfusion lengths may be engineered to dimensions that correlate to specific sterilization cycle parameters such that one housing may be used for multiple different cycle types within a facility.

FIG. 6b depicts a side view (showing first housing edge 56). Retainer 66 retaining carrier 30 can be seen traversing all three perfusion channels 14, 15, and 15b. Open ends 16 are in fluid communication with the environs. In the embodiment depicted, perfusion channels 14, 15, 15b are of three different heights. In other embodiments the channels may have substantially identical heights. In yet other embodiments, some channels may be substantially identical to each and different from others. Any conceivable combination of channel heights (and lengths) are within the scope of the present disclosure. Those of skill on the art will recognize that channels may be dimensioned as necessary to monitor sterilization adequacy to accurately assess any particular sterilization cycle.

FIGS. 7a-d depict end views of another embodiment of the sterilization monitoring device according to the present disclosure. In this embodiment, sterilization monitoring device 10 comprises a perfusion channel 14 and a chemical indicator carrier retainer 66. Retainer 66 retains carrier 30 in fluid communication with perfusion channel.

Perfusion channel 14 is formed of single molded piece. Molded piece is typically formed of a material that is substantially impermeable to sterilant and also rigid enough to maintain the shape and dimensions of perfusion channel.

An upper portion 70 comprises a laterally extending portion 74 that forms ceiling 20 portion 20 of perfusion channel 14 and defines width of perfusion channel 14. Two vertical edges descending downward from laterally extending portion 74 form perfusion channel side walls 22a, 22b and define the height the perfusion channel 14. In the embodiment depicted, two portions extend laterally from the bottom of side walls 22a, 22b defining upper carrier contacting regions 80, 82.

Figure 7A:
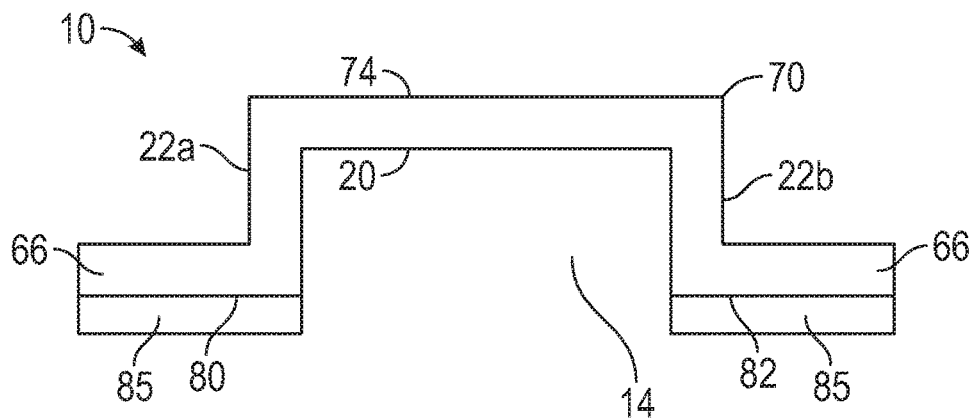
FIG. 7a is an end view of an embodiment of the sterilization monitoring device according to the present disclosure.
Figure 7B:
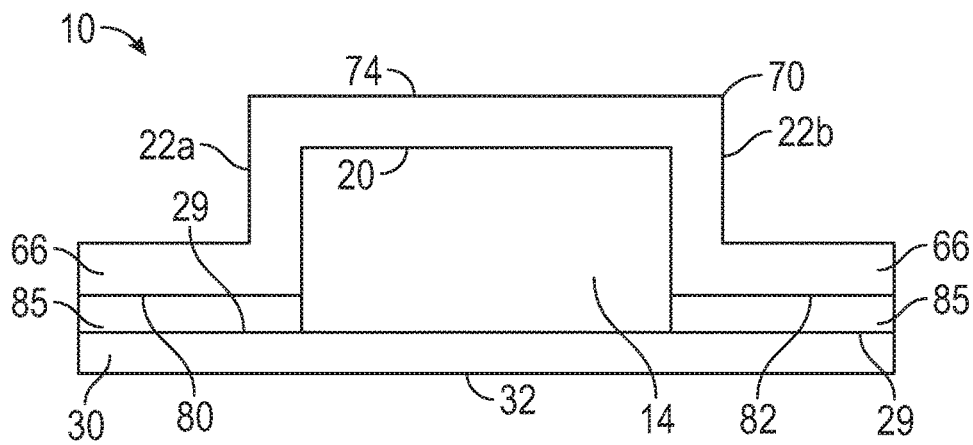
FIG. 7b is an end view of an embodiment of the sterilization monitoring device according to the present disclosure.

Upper carrier contacting regions 80, 82 are configured to contact an upper surface 29 of the carrier 30. At least a portion of the upper contacting regions 80, 82 may be provided with an adhesive 85 for securing carrier 30 thereto. Adhesive may be a pressure sensitive adhesive (PSA). Suitable PSAs typically are non-reactive and impervious to the sterilant. Pressure sensitive adhesives are well-known and suitable PSAs may be readily selected by those of skill in the art. PSA acts to hold carrier 30 in fluid communication with the perfusion channel 14 as depicted in FIG. 7b.

Figure 7C:
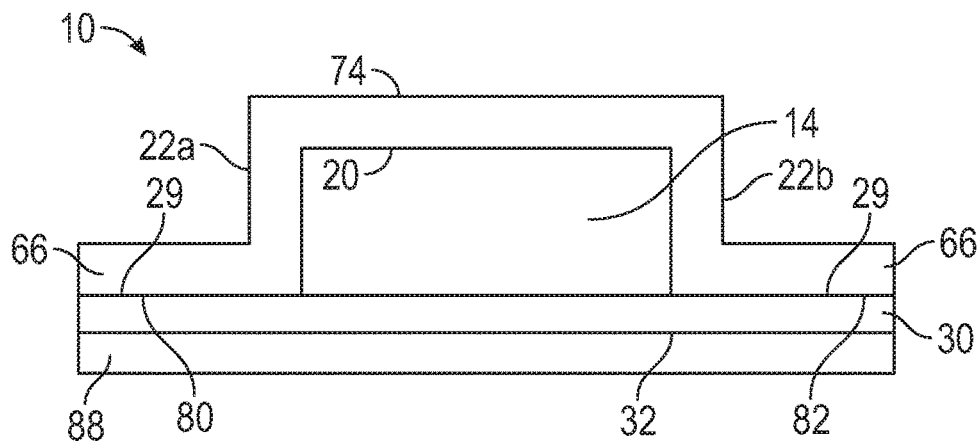
FIG. 7c is an end view of an embodiment of the sterilization monitoring device according to the present disclosure.

In the embodiment depicted in FIG. 7c, carrier 30 is shown to be retained within retainer 66. Upper carrier contact regions 80, 82 are contacting upper surface 29 of carrier 30. In some embodiments bottom portion comprises adhesive as described above. In other embodiments, bottom portion is free of adhesive. This embodiment is substantially similar to that depicted in FIGS. 7a-b, with the addition of a laminating film 88 disposed across backing 32 of carrier. Laminating film 88 may be provided with an adhesive on the carrier contacting portion (not shown), and laminating film 88 may be substantially impermeable to sterilant.

Figure 7D:
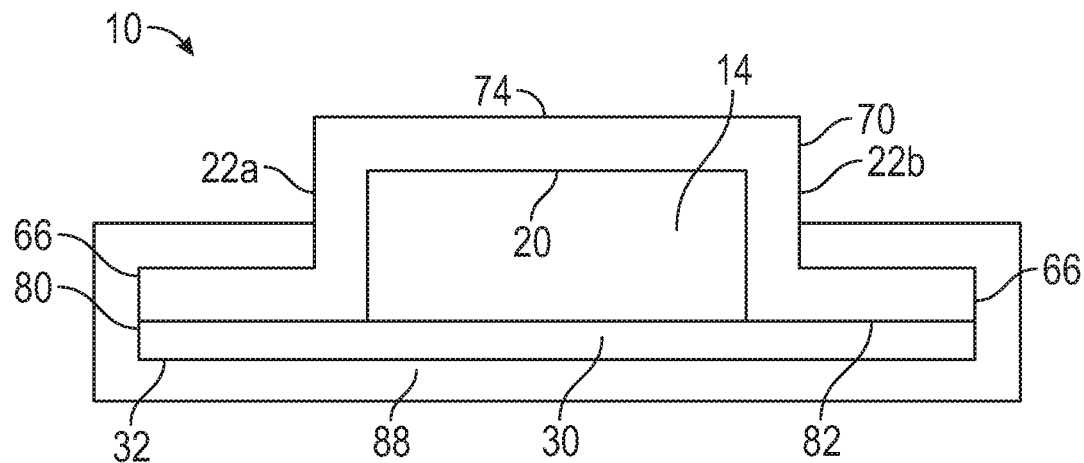
FIG. 7d is an end view of an embodiment of the sterilization monitoring device according to the present disclosure.

In yet other embodiments, laminating film 88 may extend over portions of the upper portion 70 as depicted in FIG. 7d. For example, laminating film may extend around edges over top tops of the laterally extending edges comprising the upper carrier contacting regions 80, 82. In other embodiments, laminating film 88 may extend to cover entire upper portion (not shown).

Figure 7E:
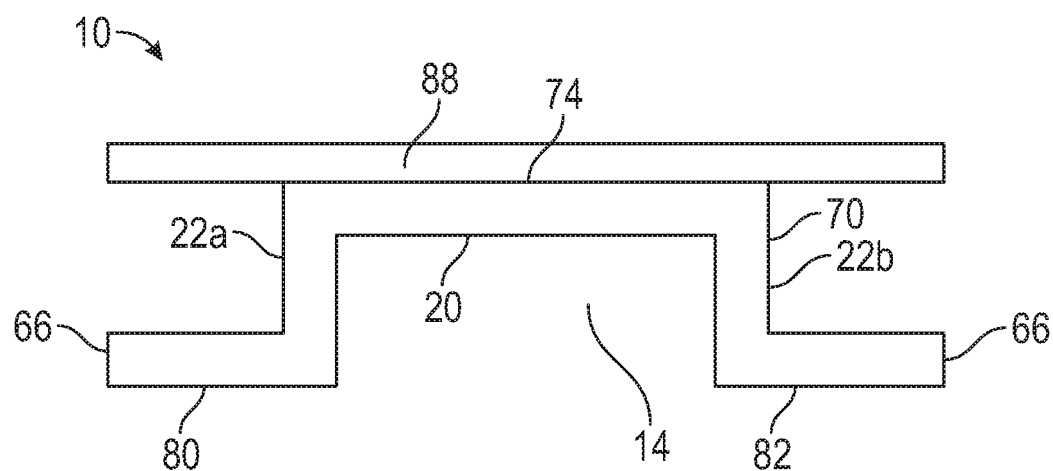
FIG. 7e is an end view of an embodiment of the sterilization monitoring device of according to the present disclosure.

As shown in FIG. 7e, sterilization monitoring device 10 may be provided as a pre-assembled unit with laminating film adhered to upper portion at an approximate center of the laminating film 88. Unadhered portions are shown extending laterally outward, which are adhered to contours of upper portion and around underside of carrier after carrier is joined to device 10 (not shown) via upper carrier contacting regions 80, 82.

Figure 8:
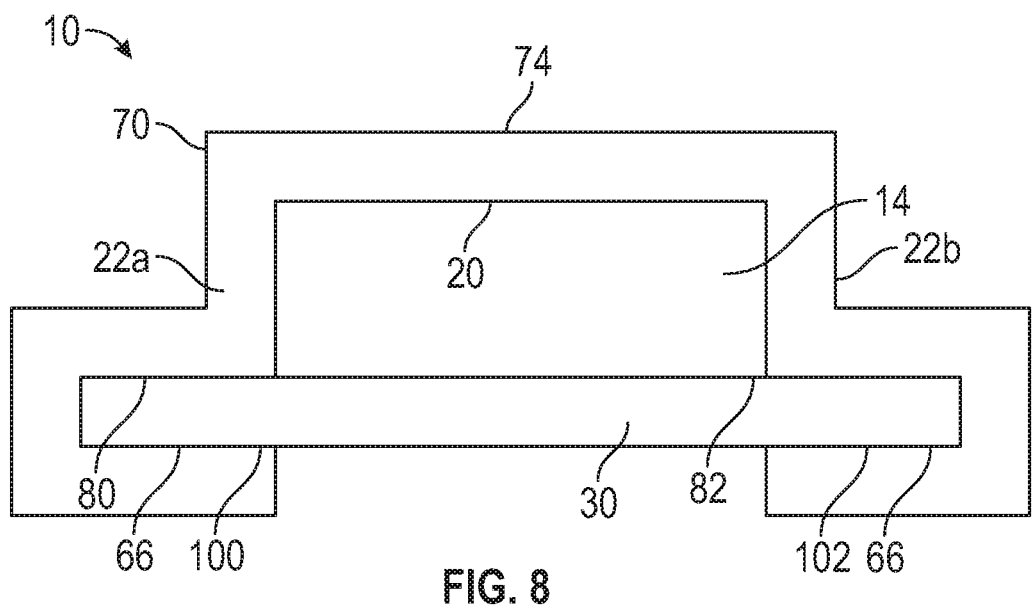
FIG. 8 is an end view of an embodiment of the sterilization monitoring device according to the present disclosure.

FIG. 8 depicts an end view of yet another embodiment of the sterilization monitoring device of the present disclosure. In this embodiment, sterilization monitoring device 10 comprises a perfusion channel 14 and a chemical indicator carrier retainer 66. Retainer 66 retains carrier 30 in fluid communication with perfusion channel 14.

Perfusion channel 14 is formed of single molded piece. Molded piece is typically formed of a material that is substantially impermeable to sterilant and also rigid enough to maintain the shape and dimensions of perfusion channel.

An upper portion 70 comprises a laterally extending portion 74 that forms ceiling portion 20 of perfusion channel 14 and defines width of perfusion channel 14. Two vertical edges descending downward from laterally extending portion 74 form perfusion channel side walls 22a, 22b and define the height the perfusion channel 14. In the embodiment depicted, two portions extend laterally from the bottom of side walls 22a, 22b defining upper carrier contacting regions 80, 82.

Retainer 66 of sterilization monitoring device according to this embodiment comprises at least one lower carrier contacting region. In the embodiment depicted, upper portion 70 includes two vertically descending portions 94, 96 that comprise two lower carrier contacting regions 100, 102. Lower carrier contacting regions 100, 102 substantially align with upper carrier contacting regions 80, 82 to sandwich carrier 30 therebetween. One, two, or more contacting regions 80, 82, 100, 102 may comprise adhesive (not shown) as described above. In some embodiments, upper carrier contacting regions 80, 82 comprise adhesive (not shown). On other embodiments lower carrier contacting regions 100, 102 comprise adhesive (not shown). In yet another embodiment, all contacting regions 80, 82, 100, 102 comprise adhesive (not shown). In yet other embodiments, all surfaces are free of adhesive. In these embodiments, retainer 66 is dimensioned to provide a tight fit about carrier 30. Regardless of the particular embodiment, retainer 66 is typically configured to substantially prevent perfusion of sterilant therethrough.

Figure 9:
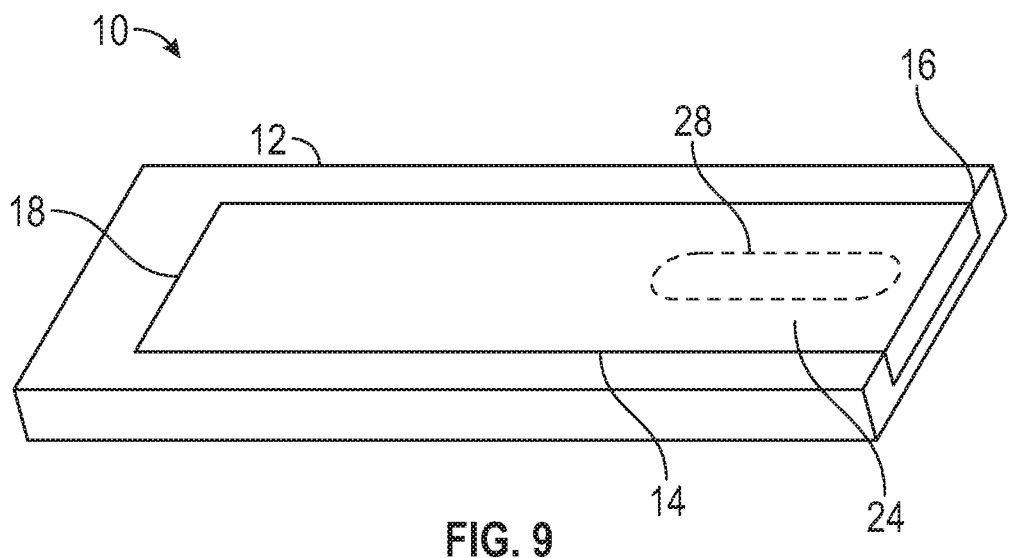
FIG. 9 is a perspective view of an embodiment of a sterilization monitoring device with a chemical indicating composition carrier disposed within the channel according to the present disclosure.

In each embodiment of the present disclosure, each perfusion channel is fluidly associated with a chemical indicating composition appropriate for the sterilant to be employed in the sterilization cycle that will be monitored by the sterilization monitoring device 10. In the embodiment shown in FIG. 9 chemical indicating composition 28 is shown to be disposed in an oval shape near the first end 16 (which is open to the environs). As will be appreciated, the chemical indicating composition 28 may be disposed in any shape, size, and location along the perfusion channel 14. In the embodiment depicted, chemical indicating composition 28 is disposed on the floor portion 24 of the sterilization monitoring device 10.

In some embodiments, the chemical indicating composition 28 may be provided separately on a carrier or substrate. In these embodiments, the carrier may be inserted into the perfusion channel 14 (shown in FIG. 11) prior to the sterilization cycle. These embodiments advantageously allow the sterilization monitoring device to be reused and/or may simplify the manufacturing process.

Figure 10A:
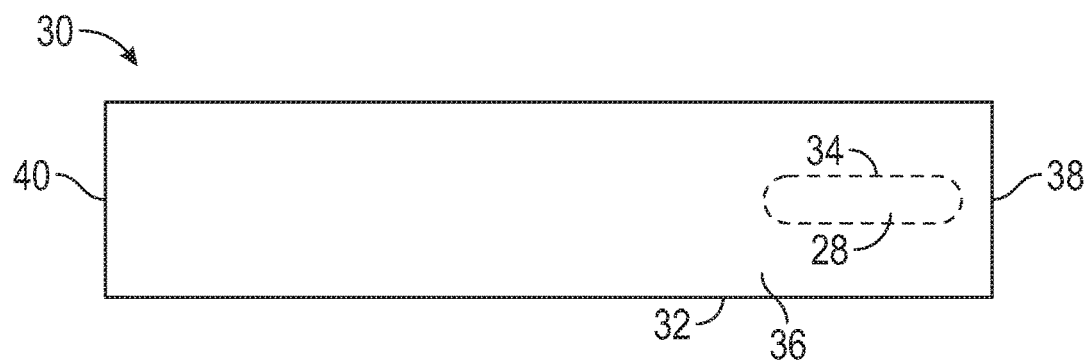
FIGS. 10a-d are top views of various embodiments of chemical indicating composition carriers according to the present disclosure.
Figure 10B:
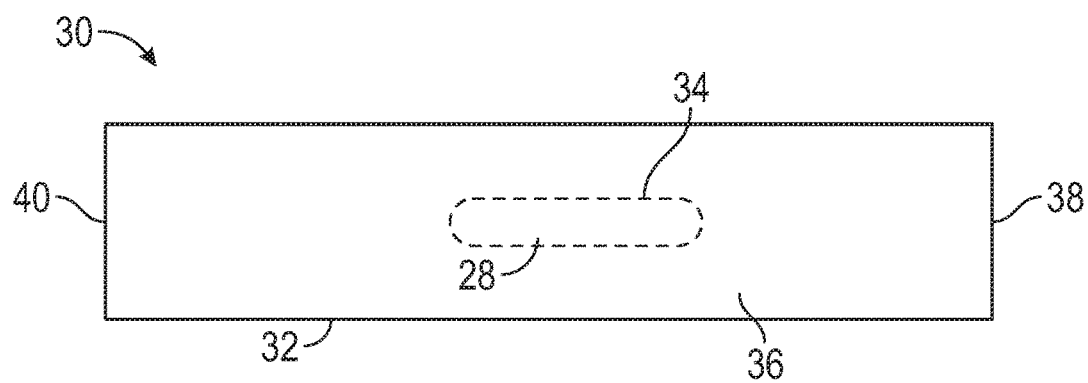
Figure 10C:
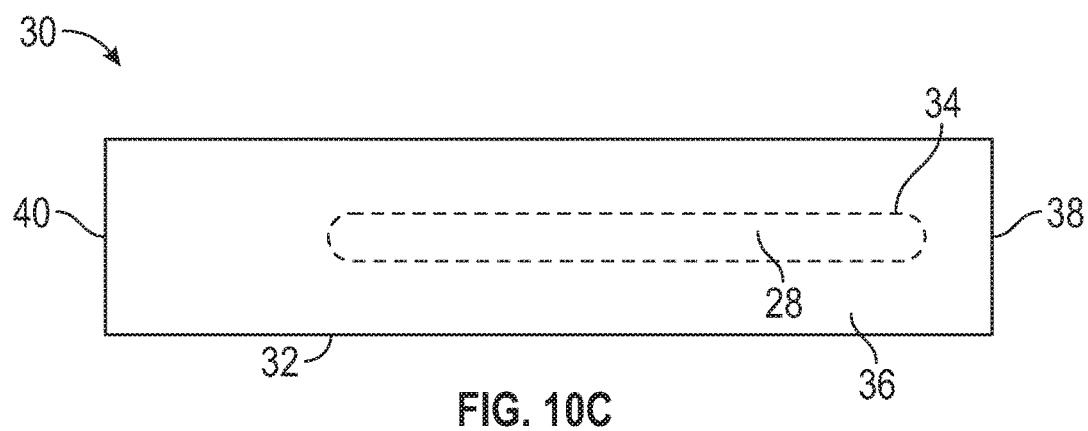
Figure 10D:
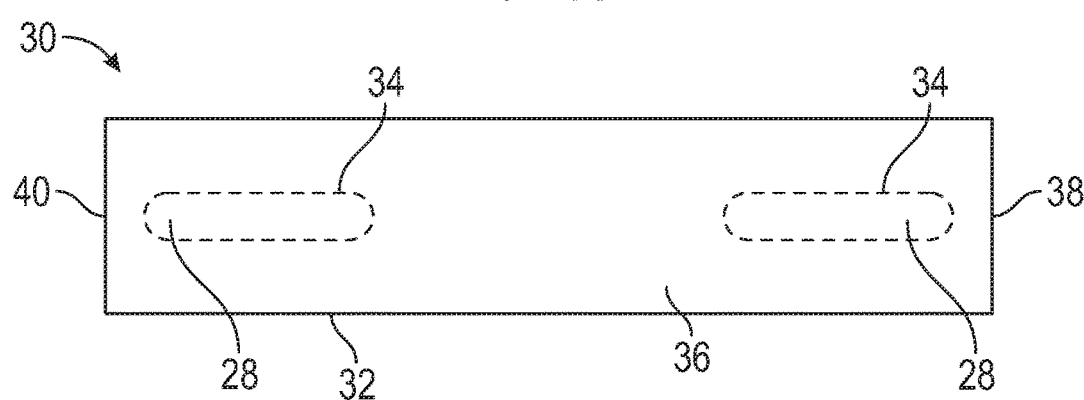

Carriers for chemical indicating compositions are referred to colloquially as "test strips" and the term will be used interchangeably with "chemical indicating composition carrier" herein. An example of a chemical indicating composition carrier is the Comply™ 1251 EO Chemical Indicator Strip available from 3M of St. Paul, MN. Various embodiments suitable for use with the present sterilization monitoring device are illustrated in FIGS. 10a-d. Test strips 30 typically have a backing or carrier 32 having a front surface upon which a chemical indicating composition 28 is disposed within a printed region 34. A portion of the front surface may remain unprinted, that is, free of chemical indicating composition as an unprinted region 36. The front surface may include markings such as branding and/or indicia useful for interpreting results. Backing 32 has a first end 38 and a second end 40. As illustrated in the Figures, the printed region 34 can vary in placement with respect to the first and second ends 38, 40, respectively. For example, in FIG. 10a, printed region 34 is biased toward the first end 38. FIG. 10b depicts an embodiment with the printed region 34 existing approximately midway between the first end 38 and the second end 40. Printed region 34 can extend for longer lengths across backing 32 as shown in FIG. 10c. In some embodiments, the printed region 34 extends substantially from first end 38 to second 40 (not shown). Multiple printed regions 34 may be provided as shown in FIG. 10d. The configuration of chemical indicating composition on the chemical indicating composition carrier 30 is not limiting. Any conceivable configuration is within the scope of the present disclosure. It will be appreciated by those of skill in that art, that test strips may be designed to meet any particular needs with respect to sterilization monitoring device configuration and/or sterilization cycle parameters.

The chemical indicating composition of the sterilization monitoring device of the present disclosure may comprise one or more dye and pigment that changes from one color to another color (including from colorless to colored, or vice versa) upon interaction with the sterilant. For steam sterilant, a typical interaction of the indicator with the sterilant involves production of sulfur anions that react with lead or another metal to make a black metal sulfide. For ethylene oxide sterilant, a typical interaction of the indicator with sterilant involves reaction of a dye or pigment with ethylene oxide directly, which results in a color change. Another approach for indication of ethylene oxide involves use of an indicating composition that contains a metal salt, reaction of which with ethylene oxide results in a pH change that can be detected by a dye that is a pH indicator. For VHP sterilant, a typical interaction of the indicator with sterilant involves oxidation of the indicator dye or pigment. Another approach involves oxidation of a metal salt to generate highly reactive oxygen radicals that subsequently react with the dye or pigment. The chemical indicating composition of the present disclosure may contain more than one dye or pigment, or a mixture of one or more dye and one or more pigment. An example of a mixture of a dye and a pigment is an indicating composition that contains a pigment that is stable to interaction with hydrogen peroxide and a dye that reacts with hydrogen peroxide. For example, a red pigment can be combined with an excess amount of blue dye to make a predominately blue chemical indicating composition. Upon interaction with VHP, the blue composition turns pink due to bleaching of the blue dye (to colorless) by the action of hydrogen peroxide, thus revealing the red pigment. In some embodiments, the dye or pigment is chosen from methane, monoazo, diazo, triazo, diazine, thiazine, cyanine, xanthene, oxazine, anthraquinone, benzodifuranone, phthalocyanine, quinophthalone, and nitro- and nitroso colorants and combinations thereof.

An overcoat may be applied to the chemical-indicating composition. Such an overcoat may diminish or augment the reactivity of the indicating composition to sterilant gas. For example, an overcoat containing a compound capable of oxidation, such as mercaptobenzothiazole, slows the reaction of hydrogen peroxide with the indicating composition. The overcoat may also reduce the potential for transfer of the chemical indicating composition to instruments that may contact the chemical indicator of the present disclosure before, during, or after sterilization. A number of compositions may be used as an overcoat. For example, ethylcellulose can be the overcoat material.

The chemical indicating composition may be disposed in fluid communication with the perfusion channel 14 using any convenient technique known to those of skill in art, such as, e.g., printing or coating method, including ink jet printing, knife coating, gravure coating, flexographic coating, etc.

In one embodiment, the moving front is a visible depiction of the reaction products of the chemical indication composition with the sterilant in the perfusion channel.

Figure 11:
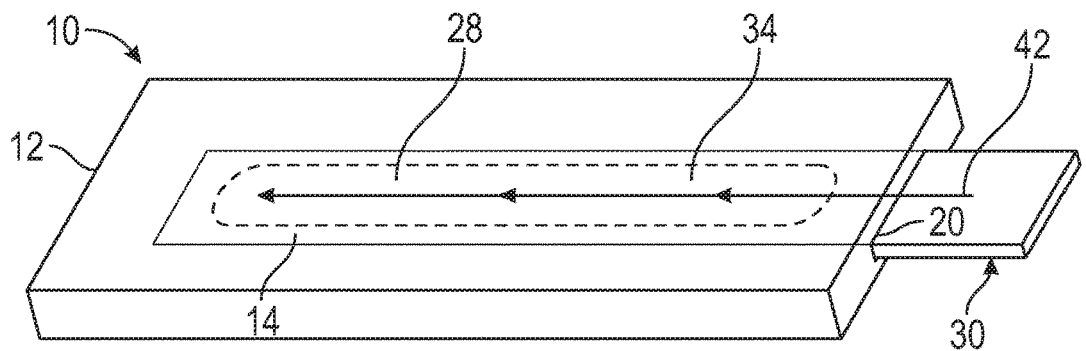
FIG. 11 is a perspective view of an embodiment of a sterilization monitoring device with chemical indicating composition carrier disposed therein.

FIG. 11 is a perspective view of an embodiment of the sterilization monitoring device 10 shown with a chemical indicating composition carrier 30 inserted. In the embodiment shown, printed region 34 comprising chemical indicating composition 28 is shown to extend laterally along substantially the entire perfusion channel 14 length. As already detailed, printed region 34 can take on any variety of configurations. Chemical indicating composition carrier 30 extends outwardly from perfusion channel 14 for ease of insertion and removal. Additionally, in some embodiments, chemical indicating composition 28 is provided on a surface of the sterilization monitoring device 10 itself, thus eliminating the need for a test strip.

The perfusion channel 14 height (shown in FIGS. 2 and 3) is greater than the height of the chemical indicating composition carrier 30 such that a fluid pathway 42 bounded by the ceiling portion 20, sidewalls 22a, 22b (more clearly shown in FIG. 2) and front surface of chemical indicating composition carrier 30 is created. In some embodiments the fluid pathway extends along the entire length of perfusion channel 14. As will be detailed below, the length of fluid pathway should be sufficient to accurately monitor sterilization parameters. In embodiments employing a chemical indicating composition carrier (or other chemical indicating composition carrier), sterilization monitoring device 10 should be configured to provide a relatively tight fit for the chemical indicating composition carrier to minimize perfusion of sterilant through locations other than the open end of the perfusion channel 14.

In use, sterilization monitoring device 10 is placed within a sterilization chamber. At this point perfusion channel 14 is in equilibrium with the normal atmosphere and is filled with air. Upon initiation of sterilization cycle, as air is evacuated from the sterilization chamber, the air that occupies the perfusion channel 14 will be evacuated bringing the perfusion channel 14 into substantial equilibrium with the evacuated sterilization chamber. As sterilant is delivered into chamber and the temperature increased, the pressure within the chamber will increase relative to that within the perfusion channel 14. This increase in chamber pressure will create a pressure gradient force extending from the sterilization chamber interior to the perfusion channel causing sterilant to perfuse into the perfusion channel 14 through the fluid pathway 42 (shown as series of arrows in FIG. 11). By nature of the inventive perfusion channel, sterilant will typically perfuse into the perfusion channel 14 and flow laterally across the surface of the chemical indicating composition 28.

Advantageously, with sterilization monitoring devices 10 according to the present disclosure, the rate at which the sterilant advances through the perfusion channel 14 is related to multiple critical sterilization parameters such as, for example, duration of exposure, concentration of sterilant, and temperature.

Figure 12A:
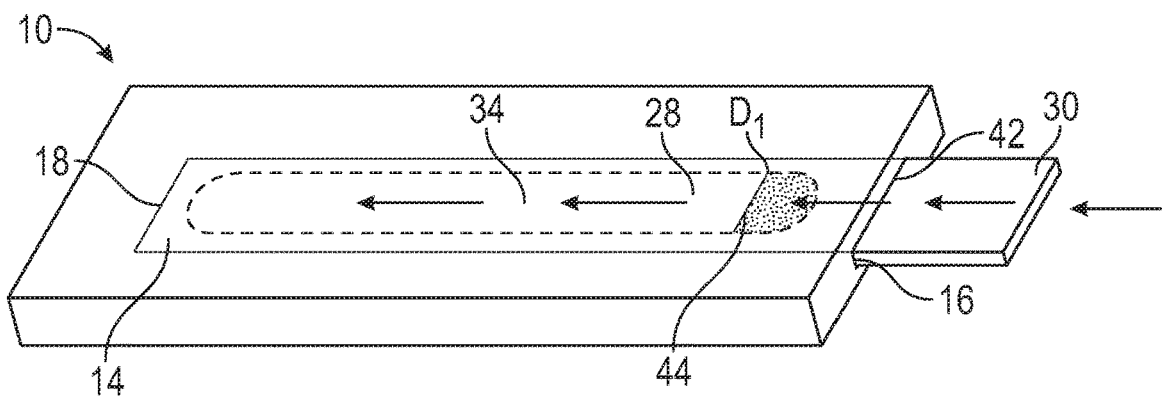
FIGS. 12a-c are perspective views of the embodiment of FIG. 8 after exposure to a sterilant for three increasing time intervals.
Figure 12B:
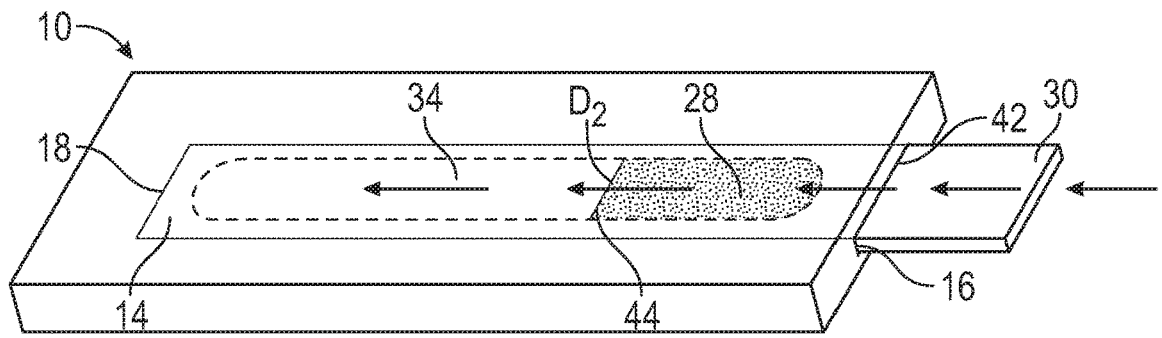
Figure 12C:
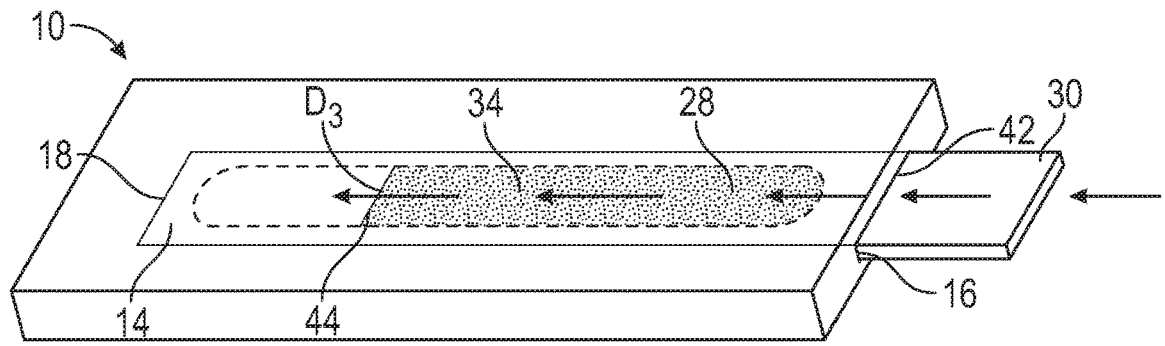

FIGS. 12a-c depict the multi-parameter monitoring feature. Sterilization monitoring device 10 of each of FIGS. 12a-c is the same device at various time points in a hypothetical sterilization cycle. It is assumed that threshold sterilant concentration and temperature (determined by particular sterilization cycle) is attained at all time points of the hypothetical sterilization cycle.

Chemical indicating composition carrier 30 carrying chemical indicating composition 28 can be seen to be disposed within perfusion channel 14 with chemical indicating composition 28 in fluid communication with sterilant perfusing through fluid pathway 42. Sterilant perfusing through perfusion channel 14 first end 16, which is in fluid communication with the environs, (i.e. an open end) in a direction away from the open end toward the perfusion channel 14 second end 18 is shown by the series of arrows. As sterilant contacts chemical indicating composition 28 a reaction occurs causing a change in the chemical indicating composition that may be detected. Typically, this change is a change in appearance, such as, for example, that is perceivable with the naked eye. Changes to chemical indicating composition may also be readable by special instrumentation if desired.

FIG. 12a is a "snapshot" of the sterilization monitoring device 10 at time, $T_1$. Shaded areas within printed region 34 represent reacted chemical indicating composition 44 that has undergone a change in appearance. At $T_1$ sterilant has perfused and reacted with chemical indicating composition to a distance, $D_1$ creating a front 44 (leading edge) of reacted chemical indicating composition 44. Distance may be measured from the edge of the of printed region 34 that is proximate to the open end (the first end 16 in the embodiment shown). Alternately, distance may be measured from any suitable point. At $T_2$, depicted at FIG. 9b, front 44 can be seen to have travelled to distance $D_2$. Similarly, at $T_3$, front 44 travels additional distance to $D_3$. As can be appreciated, perfusion of sterilant in one direction, across chemical indicating composition 28, results in a progression of appearance change (for example, color change) in a direction away from the point of entry of sterilant into the perfusion channel 14.

By controlling exposure of the chemical indicating composition to sterilant and restricting that exposure to a lateral flow of sterilant across chemical indicating composition one can advantageously monitor multiple critical sterilization parameters, such as duration, concentration of sterilant, and temperature with the present sterilization monitoring device. To accomplish this, a threshold distance of migration of the leading edge of the front 44 is correlated with sufficient values of duration, concentration of sterilant, and temperature is determined in a binomial system (i.e., pass/fail). Thus, attainment of the pre-determined distance indicates a pass while distances under the threshold indicate a fail and suggest that the instruments require additional processing to achieve adequate sterilization.

Figure 13A:
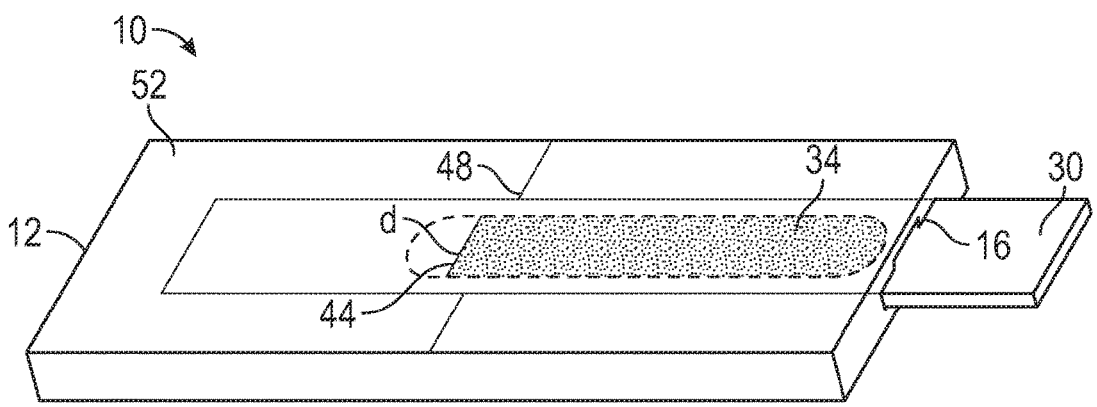
FIG. 13a-b are perspective views of the embodiment of FIG. 8 after exposure to a sterilization cycle indicating a pass condition and a fail condition, respectively.
Figure 13B:
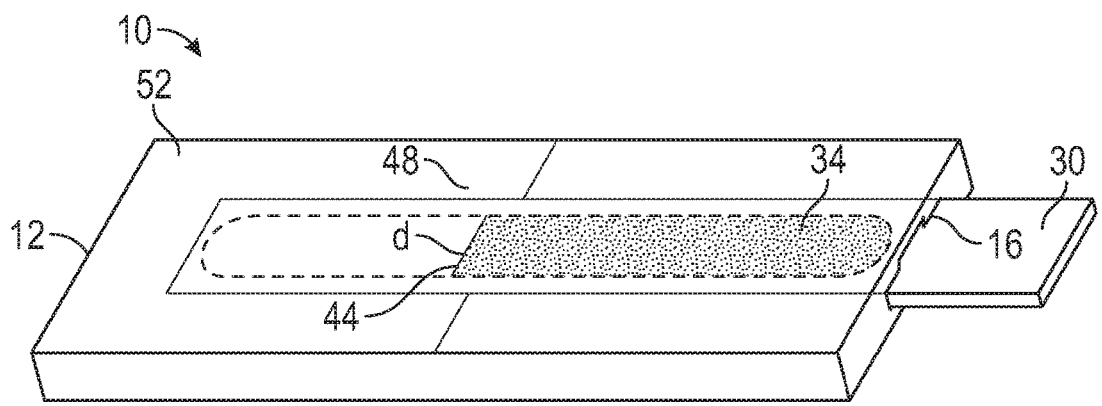

FIGS. 13a-b depict sterilization monitoring devices 10 after being subjected to a specific sterilization cycle for use to assess sufficiency of the sterilization cycle. In FIG. 13a, sterilization monitoring device 10 is shown with a reacted chemical indicating composition front 44 that has traveled a distance d from the first end 16 (the open end in this embodiment). In the embodiment shown, housing 12 includes indicia 48 to aid in interpretation of results. In this embodiment, indicia comprise hashmarks provided on the housing in a manner that is visible to a user. Hashmarks are placed at a position that represents a predetermined threshold distance of migration of the front 44 that indicates that critical sterilization parameters have been met. Therefore, if upon visual and/or instrument assisted inspection, the front 44 has traveled a distance sufficient to line up (or surpass) the indicating hashmark (shown in FIG. 13a), a "pass" is indicated and the results confirm that all critical sterilization parameters have been met. If the front 44 fails to travel at least to the hashmark 48 (shown in FIG. 13b), a "fail" is indicated and the results suggest that one or more critical sterilization parameters have not been met and therefore that additional processing is necessary to achieve sterilization of the instruments with which the sterilization monitoring device was loaded.

Other means to facilitate interpretation of results are within the scope of the present disclosure. For example, in some embodiments, a transparent window (or series of windows) may be provided on housing 12 upper portion 52. Windows may be disposed at locations that correspond to various threshold front migration distance specific to a particular sterilization cycles so that appearance of the front 44 in that window indicates a "pass" while failure for front 44 to appear in window indicates a "fail".

Figure 14:
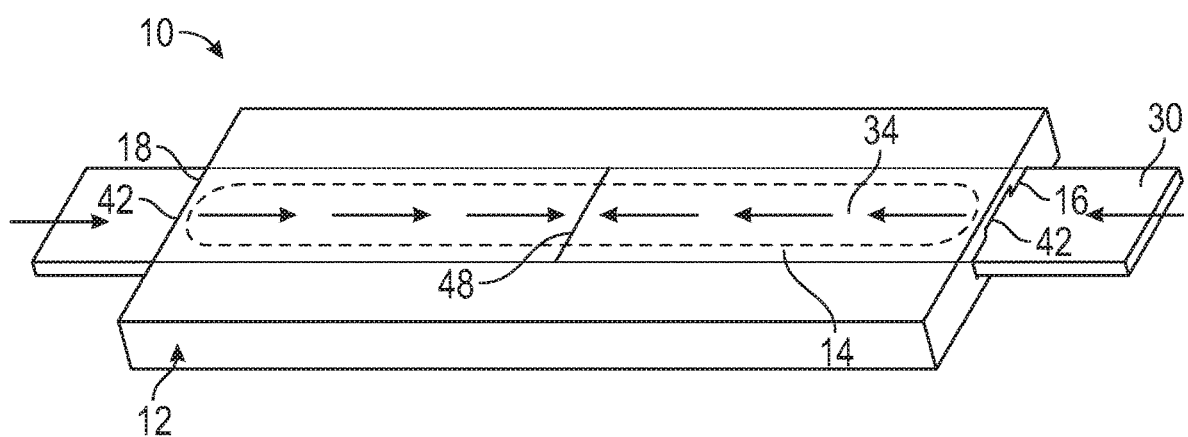
FIG. 14 is a perspective view of an embodiment of the sterilization monitoring device according to the present disclosure.

FIG. 14 depicts an alternate embodiment comprising two ends in fluid communication with the environs. As depicted with the arrows, sterilant perfuses in through both the first and second ends 16, 18 in a direction away from the open through which the sterilant entered the perfusion channel 14. This embodiment results in a moving front progressing from each of the open ends 16, 18. As exposure to the sterilization cycle progresses, the moving front originating from each end (not shown) will advance toward each other and meet at the threshold pass/fail indicator 48. Merging of two fronts advantageously produces a larger area of reacted chemical indicating composition, which may help facilitate interpretation of results. Indicia 48 in this embodiment comprise a hashmark extending across the chemical indicating composition carrier 30, which is visible through a transparent portion of the housing 12.

We claim:

1. A sterilization monitoring device comprising:
   at least one perfusion channel comprising a first end and a second end, wherein at least one of the first end or the second end are open to the environs, wherein the at least one perfusion channel further comprises a height defined by a first side wall and a second side wall extending between a ceiling portion and a floor portion, a width, and a length; and
   at least one chemical indicating composition carrier comprising at least one chemical indicating composition, wherein the at least one chemical indicating composition carrier is configured to be selectively in the at least one perfusion channel such that the at least one chemical indicating composition is in fluid communication with the at least one perfusion channel and extending along at least a portion of the at least one perfusion channel,
   wherein the at least one perfusion channel creates a laterally moving front of a sterilant across the at least one chemical indicating composition,
   wherein the at least one perfusion channel defines a fluid pathway over a top surface of the at least one chemical indicating composition,
   wherein any combination of the height, the width, and/or the length of the at least one perfusion channel are dimensioned to generate lateral movement of the sterilant from the environs through the at least one perfusion channel.

2. The sterilization monitoring device of claim 1, wherein the height and the width of the at least one perfusion channel are substantially constant along at least a portion of the length of the at least one perfusion channel.

3. The sterilization monitoring device of claim 1, wherein the at least one chemical indicating composition is substantially isolated from the environs other than through the laterally moving front created by the at least one perfusion channel.

4. The sterilization monitoring device of claim 1, wherein the first end is configured to substantially eliminate any perfusion of the sterilant into the at least one perfusion channel except for perfusion into the fluid pathway that extends laterally over a top surface of the at least one chemical indicating composition.

5. The sterilization monitoring device of claim 1, wherein a portion of an upper section of a housing forms the ceiling portion of the at least one perfusion channel.

6. The sterilization monitoring device of claim 5, wherein a lower section of the housing forms a floor portion of the at least one perfusion channel.

7. The sterilization monitoring device of claim 1, wherein the chemical indicating composition is disposed along at least a portion of the floor portion of the at least one perfusion channel.

8. The sterilization monitoring device of claim 1, wherein at least a portion of the ceiling portion forming the at least one perfusion channel is transparent.

9. The sterilization monitoring device of claim 2, wherein a distance between the first end of the perfusion channel with the chemical indicating composition defines a perfusion length.

10. The sterilization monitoring device of claim 1, wherein the at least one chemical indicating composition carrier further comprises an end being substantially aligned with the first end of the at least one perfusion channel.

11. The sterilization monitoring device of claim 1, wherein the at least one chemical indicating composition when in fluid contact with the sterilant undergoes an oxidation reduction reaction.

12. The sterilization monitoring device of claim 1, wherein the sterilant is vaporized hydrogen peroxide.

13. The sterilization monitoring device of claim 1, wherein a ratio of the width of the least one perfusion channel to the height of at least one perfusion channel is at least 4:1.

14. The sterilization monitoring device of claim 1, wherein the at least one perfusion channel defines a void space that is open to the environs.

15. The sterilization monitoring device of claim 1, wherein the sterilant is steam.

\* \* \* \* \*